(12) United States Patent
Lavrova (10) Patent No.: US 8,439,049 B2
(45) Date of Patent: May 14, 2013

(54) BRAIDED DENTAL FLOSS

(76) Inventor: Zoya Lavrova, Brooklyn, NY (US)

( * ) Notice: Subject to any disclaimer, the term of this patent is extended or adjusted under 35 U.S.C. 154(b) by 15 days.

(21) Appl. No.: 13/134,886

(22) Filed: Jun. 20, 2011

(65) Prior Publication Data

US 2011/0277783 A1 Nov. 17, 2011

Related U.S. Application Data (63) Continuation-in-part of application No. 12/455,387, filed on Jun. 1, 2009, now abandoned.

(51) Int. Cl.
*A61C 15/00* (2006.01)
*A61C 15/04* (2006.01)

(52) U.S. Cl.
USPC .......................................... 132/321; 132/329

(58) Field of Classification Search .................. 132/321, 132/323, 324, 329, 325, 326, 327, 328; 66/170, 66/169 R; 87/1, 11, 13; *A61C 15/00, 15/04*
See application file for complete search history.

(56) References Cited

U.S. PATENT DOCUMENTS

| | | | | |
|---|---|---|---|---|
| 1,285,988 A * | 11/1918 | Gudebrod | ...................... | 132/323 |
| 1,860,030 A * | 5/1932 | Hinchliff | ........................ | 28/143 |
| 2,064,074 A * | 12/1936 | McNamee | ................... | 66/169 R |
| 2,316,060 A * | 4/1943 | Fullerton et al. | ............. | 15/159.1 |
| 3,837,351 A * | 9/1974 | Thornton | ....................... | 132/321 |
| 4,007,611 A * | 2/1977 | Blezard | ............................ | 66/195 |
| 4,265,258 A * | 5/1981 | Eaton, II | ....................... | 132/321 |
| 4,523,600 A * | 6/1985 | Donovan | ...................... | 132/321 |
| 4,550,741 A * | 11/1985 | Krag | ............................... | 132/321 |
| 4,706,843 A * | 11/1987 | Thornton | ........................ | 221/48 |
| 4,836,080 A * | 6/1989 | Kite et al. | ........................... | 87/9 |
| 4,836,226 A * | 6/1989 | Wolak | ............................ | 132/321 |
| 4,974,615 A * | 12/1990 | Doundoulakis | ............... | 132/321 |
| 5,692,530 A * | 12/1997 | Bible et al. | ...................... | 132/321 |
| 5,904,152 A * | 5/1999 | Tseng et al. | .................. | 132/321 |
| 5,947,132 A * | 9/1999 | Swanson | ....................... | 132/321 |
| 5,967,154 A * | 10/1999 | Anderson | ...................... | 132/321 |
| 6,016,816 A * | 1/2000 | Ariagno | ........................ | 132/321 |
| 6,371,133 B1 * | 4/2002 | Gant | ............................. | 132/321 |
| 6,607,000 B2 * | 8/2003 | Marwah et al. | ................ | 132/321 |
| 7,152,611 B2 * | 12/2006 | Brown et al. | .................. | 132/321 |
| 2002/0100491 A1 * | 8/2002 | Antler | ........................... | 132/321 |
| 2005/0016564 A1 * | 1/2005 | Sekiya et al. | .................. | 132/323 |
| 2005/0257801 A1 * | 11/2005 | Kayser | ........................... | 132/200 |
| 2008/0230087 A1 * | 9/2008 | Blanchard et al. | ............. | 132/321 |
| 2008/0314406 A1 * | 12/2008 | Barrie | ........................... | 132/329 |

* cited by examiner

*Primary Examiner* — Robyn Doan
*Assistant Examiner* — Tatiana Nobrega
(74) *Attorney, Agent, or Firm* — Aleksandr Smushkovich

(57) ABSTRACT

A dental floss is formed as a strand, including threads braided with each other in a multi-looped manner so that forming knobs connecting adjacent quasi-flat sections that, while being stretched in a straight line, are sequentially disposed and twisted relatively to each other, whose cross-sections can be approximated to a rectangle-like figure having a width and a height greater than the width. The heights of two adjacent quasi-flat sections are disposed at a predetermined angle to each other. Due to particular braiding, the quasi-flat cross-sections and the knob's cross-section encompass different numbers of thread pieces, forming a multi-planar surface with bulges, thereby providing for a unique adhesive property increasing the floss cleaning power, grabbing and removing plaque particles from the tooth surface more efficiently than the conventional ones. It's exemplarily produced by means of adapted overlock machines, of polyester, colored, flavored, un-waxed, waxed, or impregnated with specific therapeutic agents.

9 Claims, 10 Drawing Sheets

BRAIDED DENTAL FLOSS

CROSS-REFERENCE TO RELATED APPLICATIONS

This U.S. patent application is a continuation-in-part application of a U.S. patent application Ser. No. 12/455,387, filed on Jun. 1, 2009 now abandoned, entitled "Multifilament Braided Dental Floss", hereby incorporated by reference in its entirety, and claiming priority of the U.S. patent application Ser. No. 12/455,387 within the limits of disclosure thereof. The U.S. patent application Ser. No. 12/455,387 is hereby expressly abandoned.

STATEMENT REGARDING FEDERALLY SPONSORED RESEARCH OR DEVELOPMENT

Not Applicable

THE NAMES OF THE PARTIES TO A JOINT RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION (I) Field of the Invention

The present invention relates to the oral care field, particularly to multi-filament floss devices with particular braided patterns.

(II) Description of Related Art

It is generally recognized in the dental profession that plaque, which remains on the teeth after brushing, is a major cause of tooth and gum problems. Only flossing is an effective process to remove the plaque. Without dental flossing, this plaque remains and provides a shelter for bacteria to continue metabolizing carbohydrates, excreting acid and thus attacking tooth enamel. Plaque build-ups not only lead to tooth decay and gum disease, but have been linked to other serious health problems as well.

Dental floss is a device that removes plaque and debris adhered to a person's teeth, restorations, fixed prostheses, pontics (artificial teeth), and around implants. In general, inter-proximal contact areas, whether natural or restored, have different configurations. Consequently, several types of floss devices are available to accommodate these differences. It is known that no floss on the market has received a degree of perfection that satisfies both dental professionals and consumers.

The majority of flosses currently known in the related art do not provide a sufficient quality of cleaning between teeth, mostly because they are smooth and flat. Conventional flosses do not have anchoring points which would permit an efficient pick-up and consequent removal of the food residues from the inter-proximal dental regions. Furthermore, due to the limitations in the surface topography of known flosses, there is little or no salutary massage to the gum surfaces surrounding the teeth. They provide only an inefficient means of transporting the dislodged particles from the surface which they contact with. Conventional flosses do not contact the concave surface of the radial contours of teeth in the pockets of gum dis-attachments.

Another disadvantage of the conventional dental flosses is that the gingiva is damaged due to forceful contact of the dental floss therewith. If the gingiva is in a diseased or unhealthy state, it often swells and bleeds easily, which discourages the continual use of flosses.

The conventional dental flosses are generally composed of relatively small diameter filaments woven together into single elongated strands. Most common commercial floss products are structured as a multifilament thread of different length. However, they tend to fray or split, do not have the capacity to show vividly the existence of the plaque between the teeth.

Numerous floss devices are presented in the related art. For example, there is known US Patent Application No. 2003/0154998 by Alexandre Petrocini Falleiros et. al. It refers to a texturized dental floss for interdental cleaning usually used for removing of the food debris. The floss is formed of a bundle of texturized filaments in which the filaments are unwound and then impregnated with additive composition. The texturized flosses have a higher contact surface with the inter-proximal surface of tooth and good capacity for removal of food residues. On the other hand, the texturized flosses are capable of shredding in the interproximal dental regions in which the floss may kink and bend. The texturized flosses and the floss of instant invention, also called 'Magic Floss' have completely different structures: the texturized flosses are uneven while the Magic Floss is knitted.

Another example is US Patent Application No. 2007/0144553A1 by Pamela Jill Habbard. It teaches a dental article comprising a primary strand of coated dental floss and accessory fiber of uncoated dental floss attached to the primary strand by overhand knots or other means is provided. The article provides effective cleaning of embrasures and stimulation of the gingival tissues, but its use is limited and too specific. This floss is targeted for cleaning of areas of embrasures. The Habbard's floss has specific structure and may not be employed by every consumer in everyday use.

A U.S. Pat. No. 5,063,948 teaches a bristle dental floss comprising a plurality of sub-fibers each having a plurality of bristles. Many small pieces thereof are tied to the long stands, and many of the same short pieces tied to the bristle ends. The sub-fibers, bristles, or both may be stiffened with wax; polytetrafluoroethylene (PTFE), which is commercially available under trademark Teflon®; nylon; or similar materials. The bristled dental floss has improved cleaning and massaging abilities for cleaning inter-proximal regions. Teflon® has a number of specific physical properties including great chemical and physical inertness that makes it very difficult to use the material in combination with other materials. Besides, Teflon® tends to break or rip quickly when it is stretched or pulled with pressure. Thus, Teflon® is difficult to employ in dental flossing. Bristles are attached by hitch-type knots. The aforementioned structure is complex and not easy to manufacture, which adversely affects the price and has made the invention unattractive to consumers.

U.S. Pat. No. 5,560,377 is related to improved floss comprising a composite of multifilament yarn bonded to an extruded monofilament. Both elements are made of polymer compounds, preferably nylon. The multifilament yarns can be provided in looped embodiments as a bush element or in the form of one or more tails. In the aforementioned patent, only part of the floss performs the mopping function. The multifilament thread or yarn is extruded and bonded into a monofilament using electronic welding, or gluing, or adhering, or air splicing. The aforesaid composite structure envisages the monofilament strands twisted relatively to each other along a longitudinal direction. The monofilament strands are weakly twisted, can be easy separated from each other and under tension become almost flat and smooth. Such weak structure cannot hold medications tightly between the monofilament strands.

U.S. Pat. No. 4,836,226 includes abrasive surface of either rips or dimples. This is an attempt to solve the problem of providing sufficient cleaning and removing debris from the dental textures.

U.S. Pat. No. 6,607,000 is a frilly dental floss formed of a thin wide ribbon with frilly edge or centrally located slits made of strong waxed polymer (HDPE). The taught floss has improved cleaning structure and may scoop and pull out any amount of material or plaque from within the gingival sulcus area and from the tooth surface.

There is known a texturized dental floss 'Superfloss' produced by Colgate/Palmolive Company used to clean large inter-dental spaces that have bridges and various dental prostheses. It has a greater diameter and is more effective in removing food debris. The larger diameter and the fibrous nature provide good cleaning action but in contact with saliva the floss quickly softens and loses its cleaning abilities.

U.S. Pat. No. 4,265,258 describes a relatively large diameter dental floss having a multitude of fibers overlain upon each other, in some cases extending beyond the main body of the floss. Although such a configuration provides an alternative to conventional flosses, this overlain floss could not clean the concave surface of the tooth. Furthermore, such approach provides little improvement over the conventional flosses.

SUMMARY OF THE INVENTION

(I) Objects of the Invention

A primary object of the instant invention, herein also called 'Magic Floss', is to provide an improved dental floss that delivers more effective removal of plaque and thereby results in minimization of action of the bacteria that cause tooth decay and gum disease.

Another object is to provide a dental floss that reinforces the effectiveness of bound therapeutic agents.

Another object is to provide an improved dental floss which is enhanced by pleasant flavoring and coloring.

Yet another object is to provide an endless loop floss so designed that can be engaged by the fingers of a user to assist in the flossing manipulation. Producing the endless looped floss should not require heat sealing, knotting, gluing, electronic welding, or air splicing of the floss to make the loop.

Other objects of the invention may become apparent to those skilled in the art upon learning the present disclosure.

(II) Brief Summary of the Invention

The invention provides a dental floss formed as a strand, including a plurality of multifilament thread braided with each other in a multi-looped manner so that collectively forming a volumetric knit structure; the strand, while being stretched along a straight line, has a longitudinal axis, wherein the strand comprises: a plurality of quasi-flat sections (which quasi-flat sections are herein also called 'facets') sequentially disposed and twisted in relation to each other along the longitudinal axis, wherein each such quasi-flat section is characterized with a plurality of cross-sections (herein called 'quasi-flat cross-sections') perpendicular to the longitudinal axis, wherein each such quasi-flat cross-section has a cross-sectional peripheral contour capable of being approximated to a rectangle having a width and a height, wherein the height is predeterminedly greater than the width, each such quasi-flat cross-section has a transversal axis parallel to the height, and for any two adjacent quasi-flat sections the corresponding transversal axes are disposed at a predetermined angle ALPHA in relation to each other (that provides a permanently changeable spatial orientation of the quasi-flat sections in relation to each other resulting in that the floss having a multi-planar surface), wherein each such quasi-flat cross-section encompasses a first number of thread pieces; a plurality of knobs formed between and connecting each two adjacent such quasi-flat sections, wherein each such knob is characterized with a cross-section (herein called a 'knob cross-section') perpendicular to the longitudinal axis, and encompassing a second number of thread pieces; and wherein the second number of thread pieces is greater than the first number of thread pieces. In preferred embodiments, ALPHA is substantially equal to 90 degrees.

BRIEF DESCRIPTION OF THE DRAWINGS

FIG. 16c schematically and in an enlarged scale illustrates a cross-section A-A of the piece of Magic Floss depicted on FIG. 16a.

Identical reference numerals or letters in the drawings generally refer to the same elements in different figures. A first-time introduced numeral or letter in the description is enclosed into parentheses.

DETAIL DESCRIPTION OF PREFERRED EMBODIMENTS OF THE INVENTION

While the invention may be susceptible to embodiment in different forms, there will be described in detail herein, specific embodiments of the instant invention, with the understanding that the present disclosure is to be considered an exemplification of the principles of the invention, and is not intended to limit the invention to that as illustrated and described herein.

(I) Materials, Structure, and Advantages of the Inventive Floss

According to the instant invention, the aforesaid objects, features, and advantages have been attained by designing a dental floss with a specific volumetric knit structure. The inventive volumetric knit structure of the floss factually provides for a novel teeth cleaning technology with outstanding quality.

In preferred embodiments, this floss can be made of PTFE (polytetrafluoroethylene), woolly nylon, or a combination thereof with silk, polyester, nylon, cotton, soft metallic threads or other suitable threads.

The PTFE threads are considered to have a high standard of fray and shred resistance. They can easily slide between the teeth. On the other hand, PTFE has a low coefficient of friction, which causes poor cleaning and difficulties for the consumer to hold the floss while flossing. Additionally, it is difficult to apply flavor on the PTFE threads, because they do not have an adequate surface area. These problems can be resolved by braiding the strand's threads. If the braided strand includes a plurality of knobs and facets, they become anchoring points, which increase friction, perform much better cleaning, prevent unwinding and slipping of the floss from the user's fingers. The surface of braided threads increases from 4 to 6 or more times (depending on the amount of threads) that allow easily applying flavor without wax.

The nylon monofilament is strong and does not easily break apart. It is also easily stretchable and has a capacity to take on moisture, but it does not provide the level of fray (shred) resistance as PTFE does. Woolly nylon (also known as 'texturized nylon') is very soft and gentle, and its capacity to take on moisture is greater than the capacity of regular nylon. The woolly nylon may be used for manufacturing the floss that is employed for cleaning around abutments of implants, under pontics, exposed furcations, open embrasure, and teeth adjacent to the edentulous areas. Such floss is supple, flexible, and pliant.

A combination of PTFE threads with threads made of regular nylon allows the floss accepting more flavor, due to a higher adhesion of nylon, while PTFE provides for a higher fray/shred resistance. A combination of PTFE with soft metallic threads is considered to be efficient for professional cleaning in a dental office to remove stains between the teeth.

Figure 16A:
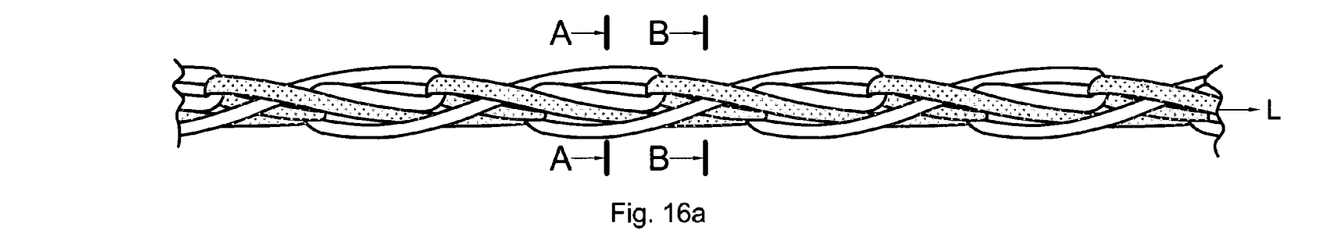
FIG. 16a schematically and in an enlarged scale illustrates a frontal view of a piece of Magic Floss, according to an embodiment of the present invention.

In preferred embodiments, a dental floss (10), shown on FIGS. 1*a*, 1*b*, 1*c*, 1*d*, and 2, formed as a strand consisting of a plurality of threads (only two such threads are depicted on FIGS. 16*a*, 16*b*, 16*c*, 16*d*, and 17) braided with each other in a multi-looped manner so that collectively forming a volumetric knit structure, which structure, while being stretched in a straight line, has a longitudinal axis (L) shown on FIG. 16*a*.

Figure 16B:
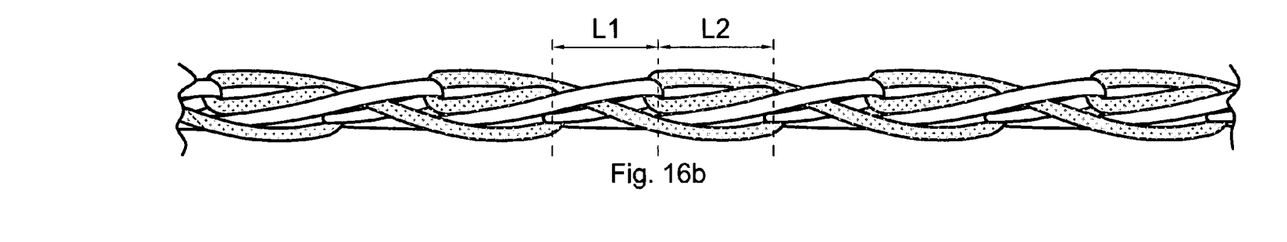
FIG. 16b schematically and in an enlarged scale illustrates a plan view of the piece of Magic Floss, according to an embodiment of the present invention.

In the 'straight-line position', the strand comprises a plurality of quasi-flat sections, e.g. (L1) and (L2), shown on FIG. 16*b*, sequentially disposed and twisted in relation to each other along the longitudinal axis L, wherein each such quasi-flat section is characterized with a number of quasi-flat cross-sections, (e.g. QF1 and QF2, shown on FIGS. 16*c* and 16*d*), being perpendicular to the longitudinal axis L, wherein each such quasi-flat cross-section has a cross-sectional peripheral contour capable of being approximated to a rectangle having a width (w) and a height (h), wherein the height h is predeterminedly greater than the width w, each such quasi-flat cross-section has a transversal axis, e.g. A1 (shown on FIGS. 16*c* and 16*d*) and B1 (shown on FIG. 16*d*), being parallel to the height h, and, for any two adjacent quasi-flat sections L1 and L2, the corresponding transversal axes A1 and B1 are disposed at a predetermined angle ALPHA in relation to each other (in preferred embodiments, ALPHA is substantially equal to 90 degrees). Each such quasi-flat cross-section A or B encompasses a first number of thread pieces, schematically shown on FIGS. 16*c*, 16*d*, and 17, e.g. to be equal to 4 thread pieces in QF1 and QF2.

Figure 17:
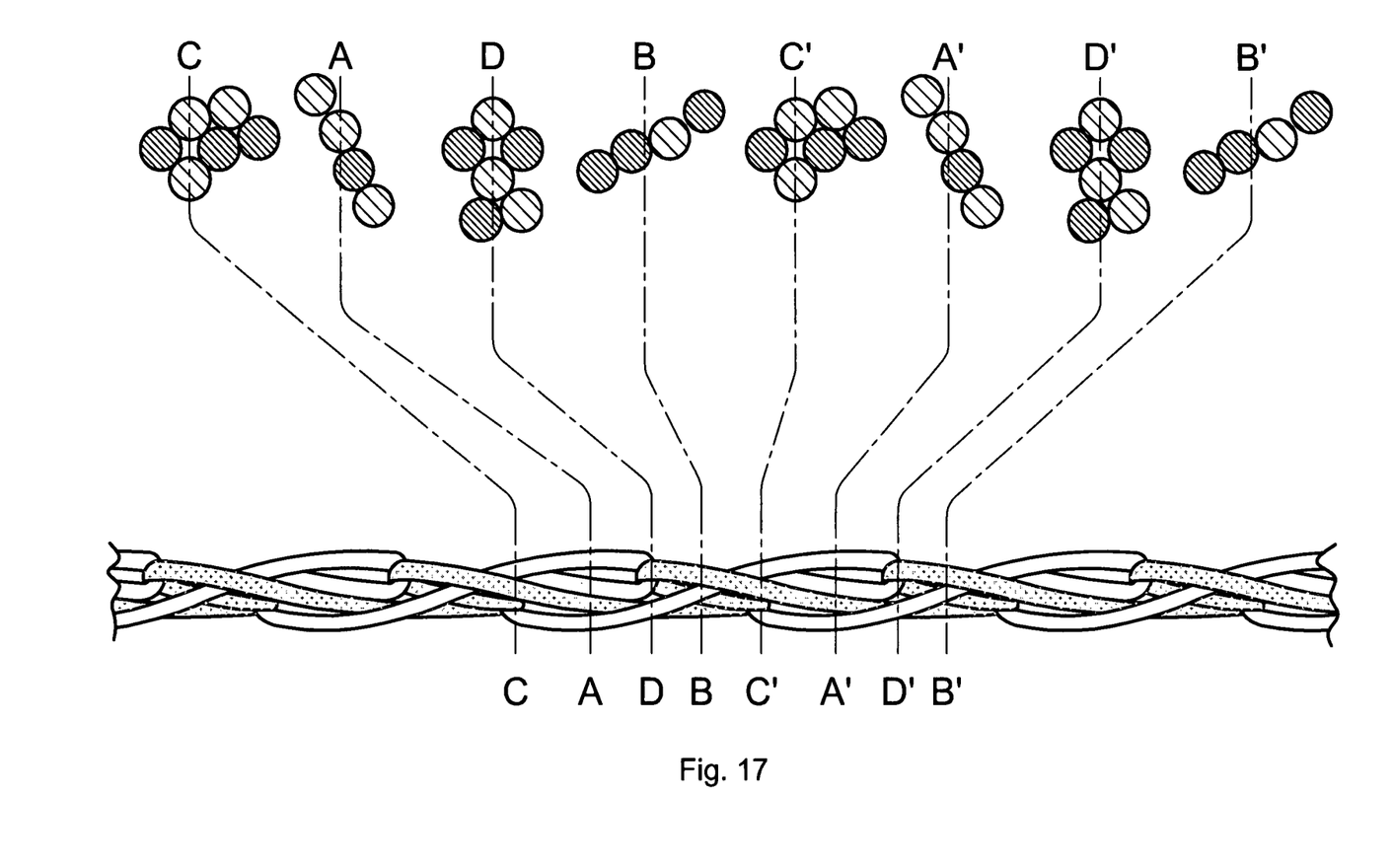
FIG. 17 schematically and in an enlarged scale illustrates a frontal view of a piece of Magic Floss with four quasi-flat cross-sections (A, B, A', B') and four knob cross-sections (C, D, C', D').

The yarn also comprises a plurality of knobs formed between and connecting each two adjacent such quasi-flat sections, e.g. L1 and L2 (FIG. 16*b*), wherein each such knob is characterized with a knob cross-section (e.g. schematically shown in a point C, or D, or C', or D' on FIG. 17), being perpendicular to the longitudinal axis L, and encompassing a second number of thread pieces (to be equal to 6 thread pieces in points C, D, C', and D', as shown on FIG. 17); wherein the second number of thread pieces (e.g. 6, FIG. 17) is greater than the first number of thread pieces (e.g. 4, FIG. 17).

The difference in the number of thread pieces between the quasi-flat cross-section and the knob cross-section is conditioned by a particular way the threads are braided: within the knob cross-section, two additional thread pieces are knitted in the opposite direction (which can be provided by the overlock sewing machines discussed herein below).

Therefore, the term 'quasi-flat section' or 'facet' is herein used to define a volumetric figure having a longitudinal axis and a quasi-flat cross-section being, at any point of the quasi-flat section, perpendicular to the longitudinal axis L, wherein the quasi-flat cross-section has a peripheral contour (cross-sectional contour) that can be (with a predetermined accuracy) approximated to a rectangle-like figure (QF1 or QF2) having a width w and a height h, and wherein the height h is predeterminedly greater (e.g. from 2 to 10 times) than the width w. According to the invention, any two adjacent quasi-flat sections have cross-sectional contours whose transversal axes (or, in fact, the respective heights being parallel to the transversal axes) are disposed at a predetermined angle ALPHA in relation to each other, thereby providing the twisting of any two adjacent quasi-flat sections at the same angle relatively to each other.

Figure 16C:
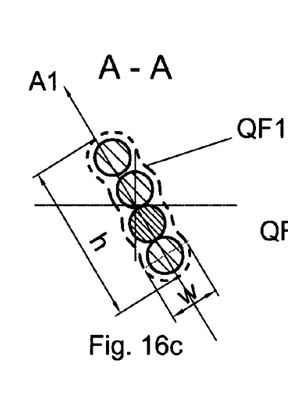
Figure 16D:
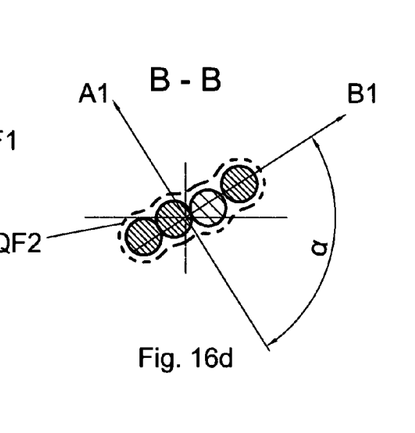
FIG. 16*d* schematically and in an enlarged scale illustrates a cross-section B-B of the piece of Magic Floss depicted on FIG. 16*a*, turned relatively to the cross-section A-A at an ALPHA angle.

Also, according to the invention, each such quasi-flat cross-section encompasses a first number of thread pieces. For instance, FIGS. 16*c* and 16*d* schematically illustrate such quasi-flat cross sections A-A and B-B. In A-A, the braiding of the threads is arranged in such a way that the quasi-flat cross section QF1 encompasses 4 thread pieces (i.e. 3 pieces of a first thread and 1 piece of a second thread). In B-B, the braiding of the strands is arranged in such a way that the quasi-flat cross section QF2 encompasses 4 thread pieces (i.e. 1 piece of the first thread and 3 pieces of the second thread). This kind of braiding is preferably provided due to the use of the overlock sewing machines discussed herein below.

Furthermore, according to the invention, each such knob cross-section encompasses a second number of strand pieces. For instance, FIG. 17 schematically illustrates such knob cross-sections: C, D, C', and D'. In these knob cross-sections, the braiding of the threads is arranged in such a way that the cross sections each encompasses 6 thread pieces (i.e. 3 pieces of the first thread and 3 pieces of the second thread). As mentioned above, this is due to the particular way the strands are braided: within the knob cross-section, two additional thread pieces are knitted in the opposite direction.

The particular design of the inventive floss that provides for the twisting of quasi-flat sections and the arrangement of knobs encompassing a greater number of strand pieces than those in the quasi-flat sections, which collectively create a unique multi-planar surface including bulges formed by the knobs thereby providing an improved adhesion of plaque to the Magic Floss that, in turn, greatly enhances the quality of cleaning the teeth.

This volumetric knit structure has an advantage in comparison with the conventional smooth floss structure in terms of delivering higher cleaning power. The aforesaid facets and knobs provide a unique cleaning property of Magic Floss that allows grabbing and removing plaque particles from the surface of tooth more efficiently than the conventional floss with a plain surface structure does. The multi-planar surface of the inventive floss along its longitudinal axis is more abrasive and less slippery than the flat floss structure. The inventive Magic Floss has a greater contact surface with the inter-proximal surface of the teeth as well as a good capacity for removing the food residues, which are usually retained in the interstices of the threads.

The improved abrasive cleaning action takes place due to: (a) the twisted arrangement of the facets that allow for cleaning the inter-proximal tooth surfaces by longitudinal movement, as well as by transverse movement, and (b) the arrangement of knobs adding non-uniformed thickness of the inventive floss. Because the material of the inventive floss is stretchable, the floss becomes 'pushable', i.e. it provides for inserting thereof into spaces generally inaccessible for conventional flosses due to the proximity of adjoining teeth.

Magic Floss maintains essentially permanent unaltered elasticity and flexibility. The facets and knobs greatly increase the cleaning and removal capacity of the inventive floss. Nonetheless, since the material of the inventive floss is soft enough, the abrasion is limited and the floss will scrub the side of the tooth while treating the gum gently. The facets and knobs are mildly depressed against the gum line and remove plaque therefrom as well. It also allows for removing more than twice as much plaque as conventional flosses do. Most un-waxed conventional flosses can occasionally fray or tear, if they are inserted into or removed from tight contacts formed by overlapping teeth, or if heavy calculus deposits or defective restorations are present. Frequent floss breakage may discourage a continuous use of the floss. The knit structure of the inventive floss prevents such breakage or fraying.

Magic Floss may be produced in a variety of colors. The colored floss provides the visual contrast with plaque and oral debris, thus enabling to see what is being removed. That allows patients to see the immediate results of flossing, and helps them to establish self-control over the process of cleaning. This increases the motivation and encourages further use of the inventive floss.

Magic Floss can be made un-waxed, waxed, flavored and impregnated with a variety of liquid therapeutic agents. Due to the volumetric knit structure, the inventive floss has a capacity to take on moisture and has enhanced lubricant characteristics due to an increase of floss surface at least from 4 to 6 times depending on the number of strands. It may contain and easily carry medications, which are useful for treatment of gum diseases and for prevention of tooth decay. Such medications may include various components, e.g. ions of fluorine, sodium laurite, sodium perborate, alantoin, myrrh extract, charcoal, and xylitol. Friction heat is often generated, when dental flosses are pulled over the teeth and especially between the teeth at the point of contact. The inventive knit structure and friction heat reinforce effectiveness of the medication components.

Flavor encourages the regular usage of dental floss. Magic Floss can be furnished with mint, orange, lemon, cherry, strawberry, vanilla, and other flavors.

Dental flossing is usually done manually when the floss is held by the fingers of both hands. Use of the floss typically involves pulling an appropriate section of the floss thread from the packaging, severance of the withdrawn section, wrapping the section's ends around two fingers on opposite hands, and then working the section in the inter-teeth spaces while maintaining it in a tight state. These manipulations require a degree of dexterity, which makes the flossing process unattractive to many people and very difficult for most children. In addition, the maintaining of tension required for effective plaque removal causes the thread to stick into and cut the user's fingers.

A device known as a 'floss holder' can assist individuals, whose functional abilities or oral architecture cannot accommodate the manual flossing. However the technique does not allow flossing under the gingival tissue without cutting the gum, and does not allow encircling the proximal surface at a required angle. The single unit floss does not permit cleaning all proximal surfaces of teeth.

For such users, an embodiment of Magic Floss in the form of 'endless loop' (or ring) with the above described volumetric knit structure can be recommended. This embodiment allows for moving the endless loop floss easily up and down between the teeth at least two times to remove soft deposits. During the flossing procedure, as one section of the floss has done its cleaning, a fresh section of the endless loop can be easily rotated into the use without the rewinding and unwinding the floss from one hand into the other. The volumetric knit structure of Magic Floss allows for making the endless loop without a knot, since such knot would be unacceptable for flossing.

There are dental flosses on the market that combine thin 'floss' portions with thick 'brush' portions coupled with a so called 'threader'. Such flosses are usually used for cleaning under pontics and between teeth with exposed roots and furcations. However, such cleaning becomes unsatisfactory because the spongy 'brush' portion turns wet from saliva and softens. This feature reduces the effectiveness of brush cleaning for such flosses. The inventive knit floss excludes this problem of losing the cleaning effectiveness while being in contact with saliva. Whether it is dry or wet, the facets of Magic Floss entrap the particles of plaque. Thusly, the invention enables consumers to achieve better overall results, inexpensively, safe, and in a much pleasurable manner.

(II) Exemplary Method and Machines for Manufacturing the Inventive Floss

According to the present invention, a preferable method for manufacturing the Magic Floss contemplates the use of an adapted conventional 'overlock' sewing machine. Generally any machines capable of adapting for braiding the inventive floss can be employed. With respect to the instant description, suitable sizes, materials, and manners of operation can be used. The inventive floss may be produced with different thickness and width. The wider and softer flosses can be used for cleaning larger surface areas (under bridges, pontics, through exposed roots and furcations). This sort of inventive floss may be recommended for cleaning implant abutments, areas with open contacts, and wide embrasures. It can also be used to remove plaque from distal aspects of the most distal teeth in all quadrants.

The following overlock sewing machines were practically used for experimental manufacturing the Magic Floss: Juki MO-2516 N class FF6-50H; Willcox and Gibbs type 504-E56-130; and Merrow Style # M-3DW-4 serial number 143548. However, any overlock sewing machine could be adapted for manufacturing this type of floss.

Because the inventive knit floss may be produced with a various thickness and width, and the machines are not used for stitching or overlocking a regular fabric, the sewing machines require some insignificant adaptation. The Juki overlock sewing machine MO-2516 N class FF6-50H was used to manufacture a finer floss, which had two needles and five threads. The adaptation was provided so that one needle and three threads were removed. In this machine, only a double chain looper worked during the manufacturing of Magic Floss, but the upper and lower loopers did not operate.

For manufacture of the inventive floss with the Willcox and Gibbs overlock machines, one of the three threads was removed with the other two threads remaining. The presser foot was also removed. The upper looper was substituted with a blind looper to produce a thinner thread chain.

For floss manufacture with the Merrow machine, no changes were required, but it produced a thicker floss to remove the plaque under bridges and the exposed furcation areas.

The machines needed readjustment of the thread tension. The tension of the side thread should be increased and the thread tension in the needle should be decreased.

(III) Exemplary Description of Preferred Embodiments of the Inventive Floss and Machines for Production Thereof As mentioned hereinabove, the inventive knit structure of Magic Floss consists of a plurality of multi-stitch facets twisted in relation to each other along the longitudinal direction of the floss at predetermined angles. FIGS. 1a, 1b, 1c, and 1d illustrate a two-dimensional picture of the volumetric structure, showing a number of sample patterns of Magic Floss: (10)A, (10B), (10C), and (10D) in an enlarged scale.

Figure 1A:
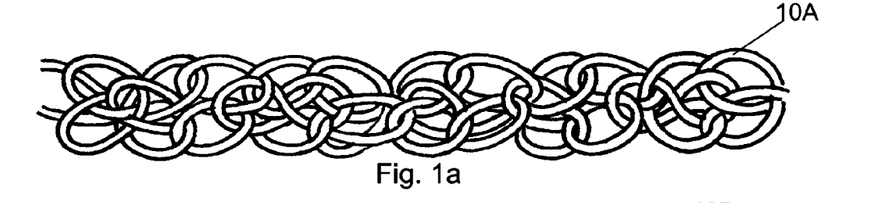
FIGS. 1a, 1b, 1c, and 1d schematically and in an enlarged scale illustrate different patterns of Magic Floss, according to embodiments of the present invention.
Figure 1B:
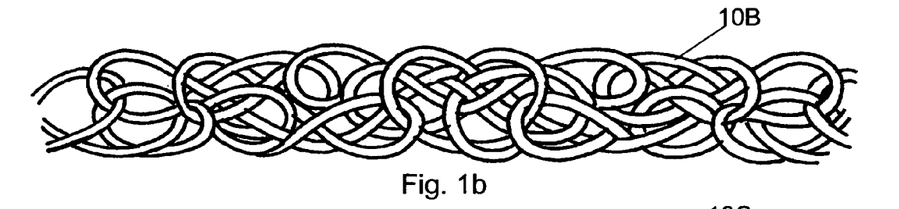
Figure 1C:
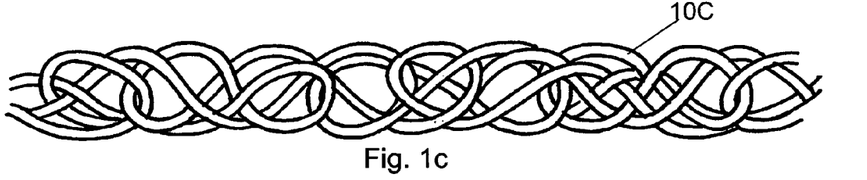
Figure 1D:
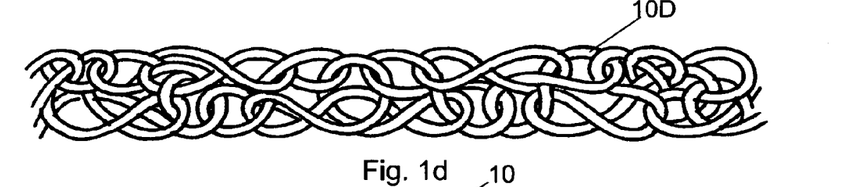
Figure 2:
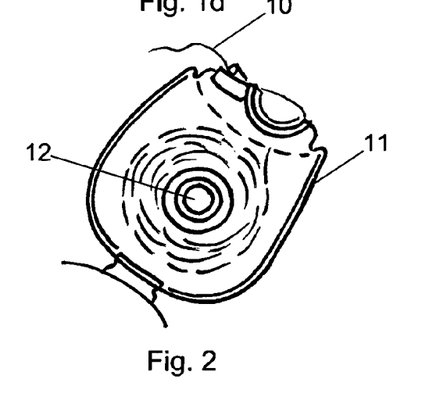
FIG. 2 schematically shows a roll Magic Floss, according to an embodiment of the present invention.

Referring to FIG. 2, there is shown a preferred embodiment of packaging for Magic Floss, wherein an inventive floss (Magic Floss) 10 is wound up on a spool (12) placed in a casing (11), having an aperture for pulling the floss 10 out of the casing 11, wherein the aperture is preferably furnished with a means (not illustrated) for cutting the floss 10.

Figure 3A:
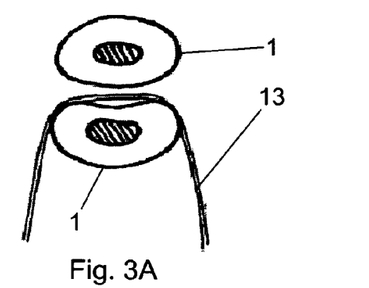
FIG. 3a shows a conventional floss positioned on the tooth's surface.

FIG. 3A depicts a conventional floss (13) positioned on the surface of a tooth (1). The picture shows the inability of the conventional floss 13 to remove bacterial plaque from a concave proximal tooth surface.

Figure 3B:
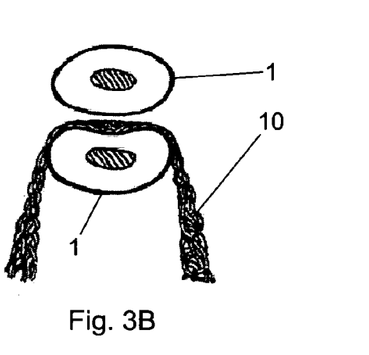
FIG. 3b illustrates the cleaning of the maxillary first premolar with Magic Floss, according to an embodiment of the present invention.

FIG. 3B illustrates the cleaning of the tooth 1 with the Magic Floss 10. It has a greater contact surface with the concave proximal tooth surface than the conventional floss 13.

Figure 4:
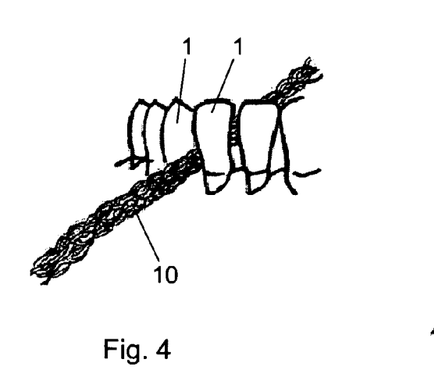
FIG. 4 illustrates the cleaning and stimulation of gingiva of embrasures with missing inter-dental papilla by Magic Floss, according to an embodiment of the present invention.

FIG. 4 shows an effective cleaning and stimulation of the gingiva of embrasures with missing inter-dental papilla between the teeth 1 and 1 by the Magic Floss 10. The floss 10 is efficient due to its unique geometry. A looped plastic structure called a 'floss threader' (not shown) can be deployed as a leader to let the floss get between the teeth or under bridges.

Figure 5:
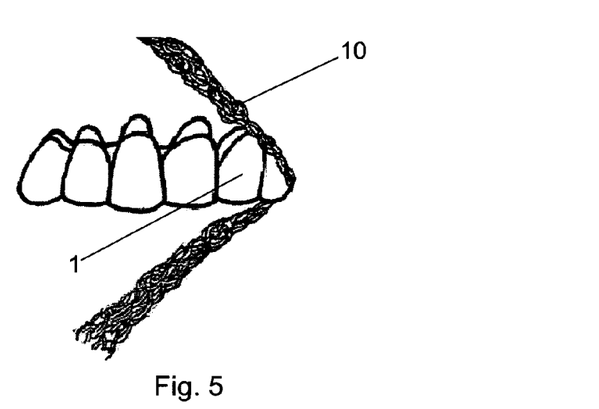
FIG. 5 illustrates the cleaning of a tooth adjacent to the edentulous area by Magic Floss, according to an embodiment of the present invention.

The cleaning of the tooth 1 adjacent to the edentulous area is depicted on FIG. 5. A 'shoe-shine stroke' can be used to remove the bacterial plaque from the surface with the floss 10.

Figure 6:
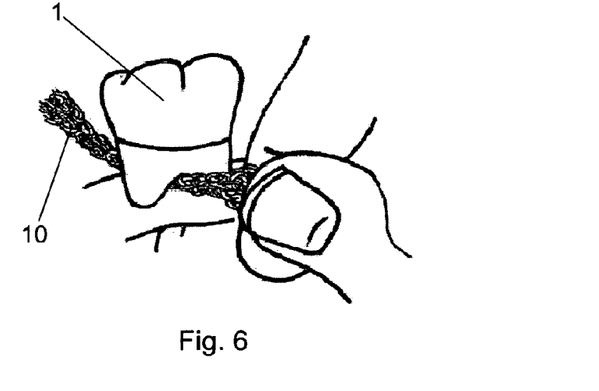
FIG. 6 illustrates the cleaning of an exposed furcating area by inserting Magic Floss and moving it back and forth, according to an embodiment of the present invention.

The cleaning of an exposed furcation area of the tooth 1 by inserting the Magic Floss 10 and moving it back and forth is shown on FIG. 6.

Figure 7:
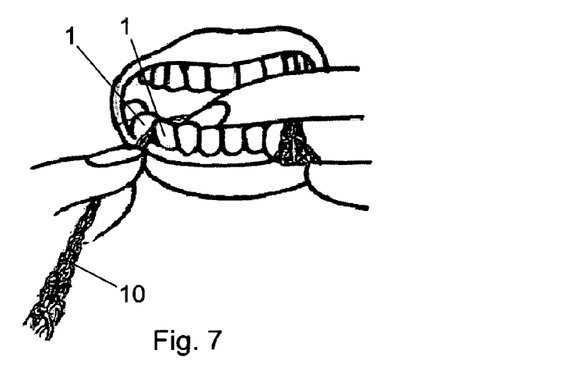
FIG. 7 illustrates Magic Floss, which can be moved all the way down to the gum line to the triangular socket, according to an embodiment of the present invention.

FIG. 7 illustrates the knit floss 10, which had reached the inter-dental space between two teeth 1. The floss 1 can be moved all the way down to the gum line to the triangular socket. The non-smooth surface of the Magic Floss area acts like tiny scoops with a brushing ability that helps in loosening and scooping away the debris of plaque retained in the interstices of the floss threads. Colored floss provides the visual contrast with plaque and debris.

Figure 8:
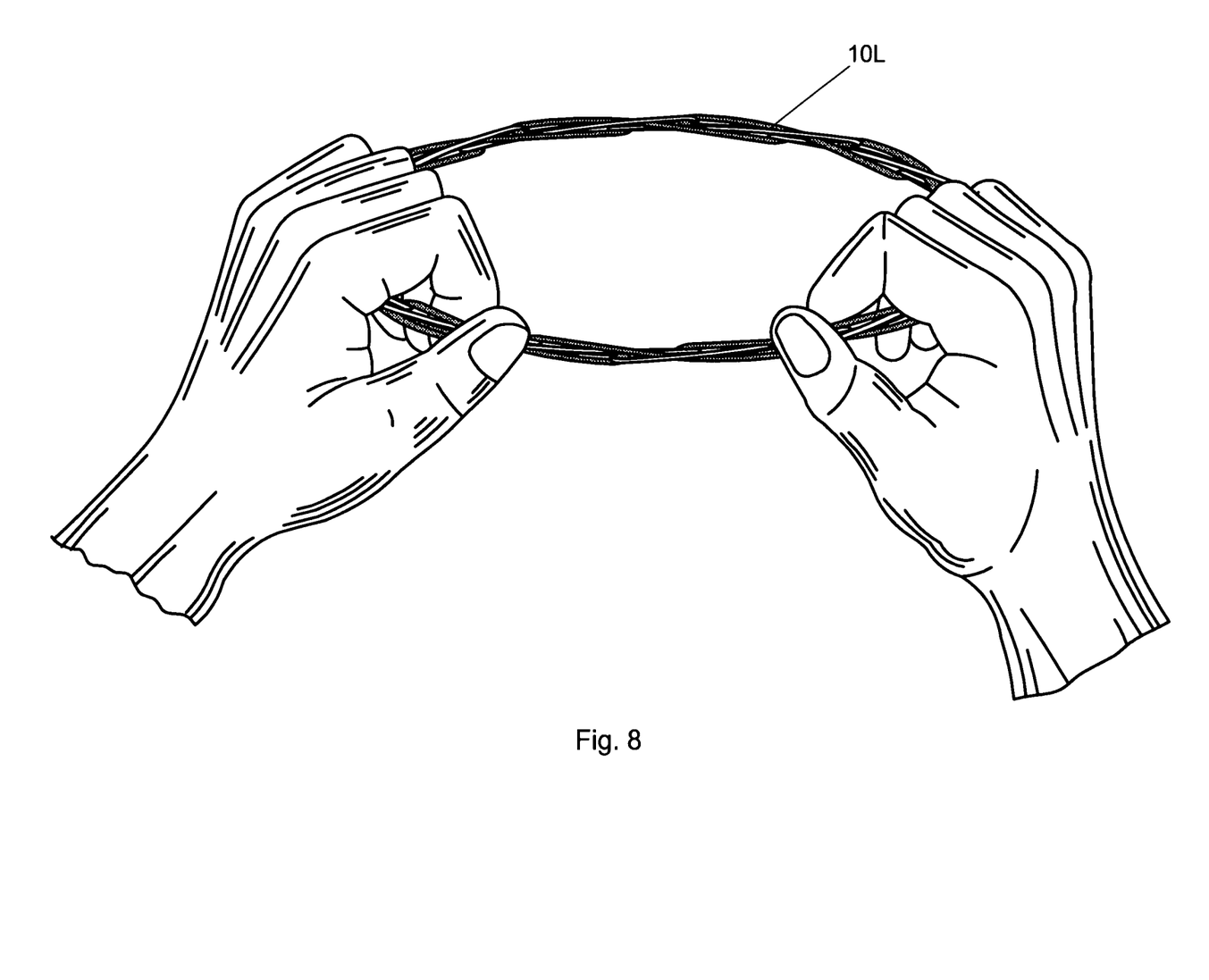
FIG. 8 illustrates the endless loop embodiment of Magic Floss, according to an embodiment of the present invention.

FIG. 8 illustrates the endless loop embodiment of Magic Floss (10L) with the knit structure without a knot. During the flossing procedure, as one section of the floss 10L has done its cleaning, a fresh section of the loop can be easily rotated into the use without the rewinding and unwinding the floss from one hand into the other.

Figure 9:
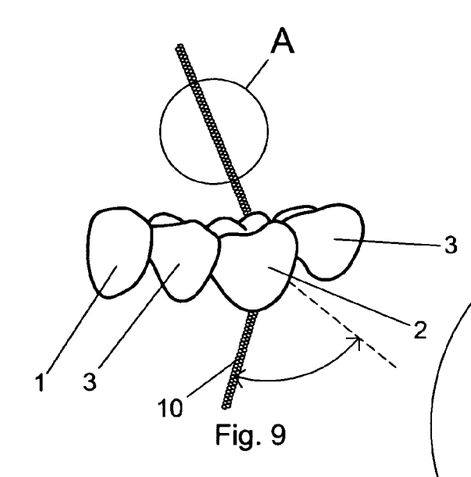
FIG. 9 illustrates the sliding of Magic Floss under a pontic, according to an embodiment of the present invention.

FIG. 9 is an illustration of the sliding of the floss 10 under a pontic (2). The floss 10 is moved back and forth several times as shown by the arrows to remove bacterial plaque from the gingival surface of the pontic 2, disposed between two crowns (3) next to a tooth 1.

Figure 10:
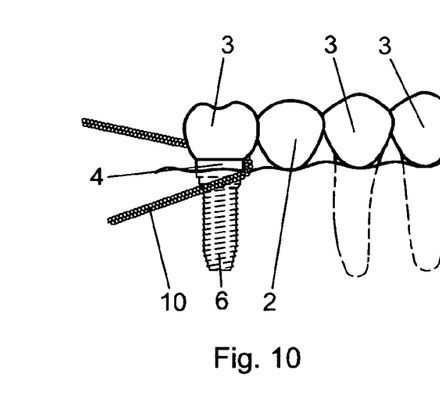
FIGS. 10 and 11 illustrate the cleaning around abutments, according to an embodiment of the present invention.

FIG. 10 illustrates the cleaning around an abutment (4) located under a crown 3 disposed next to a pontic 2. The abutment 4 is coupled with an implant (6).

Figure 11:
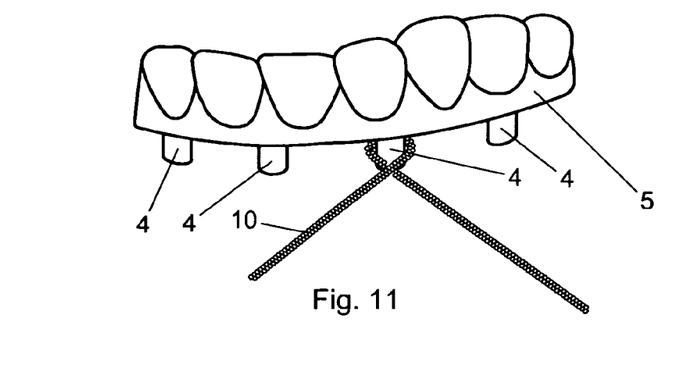

FIG. 11 illustrates the cleaning with Magic Floss 10 around an abutment 4, which supports a full denture (5) with other three abutments 4.

Figure 12:
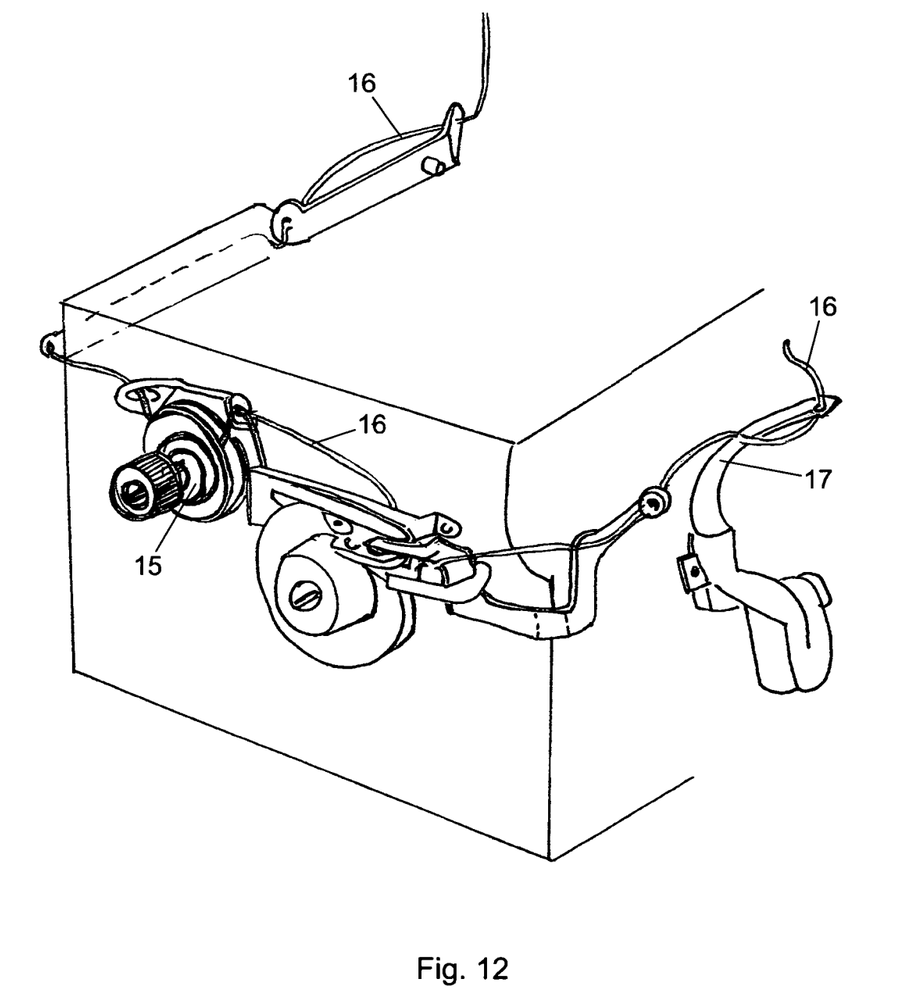
FIG. 12 shows a fragment of an overlock sewing machine for manufacturing Magic Floss, according to an embodiment of the present invention.

FIG. 12 shows detail parts of a common overlock sewing machine: a thread tension nut (15) used for adjustment of the tension of a side thread (16). The machine should be adapted for manufacturing the Magic Floss, particularly: only one double-chain looper (17) is to be used.

Figure 13:
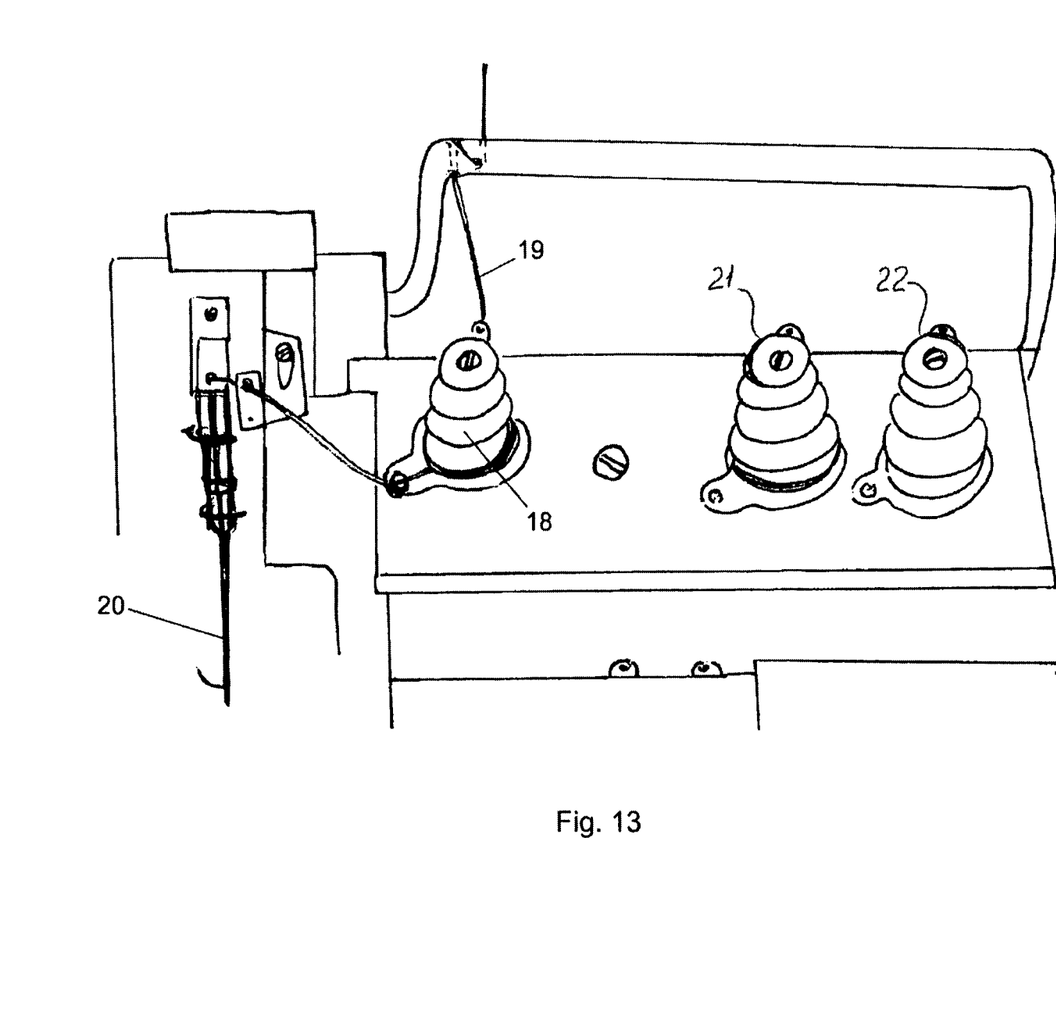
FIG. 13 shows another fragment of an overlock sewing machine for manufacturing Magic Floss, according to an embodiment of the present invention.

FIG. 13 depicts detail parts of a common overlock sewing machine: a thread tension nut (18) used for adjustment of the tension of a thread (19) in a needle (20). The machine should be adapted, particularly: tension nuts (21) and (22) are not used, i.e. threads are removed therefrom.

Figure 14:
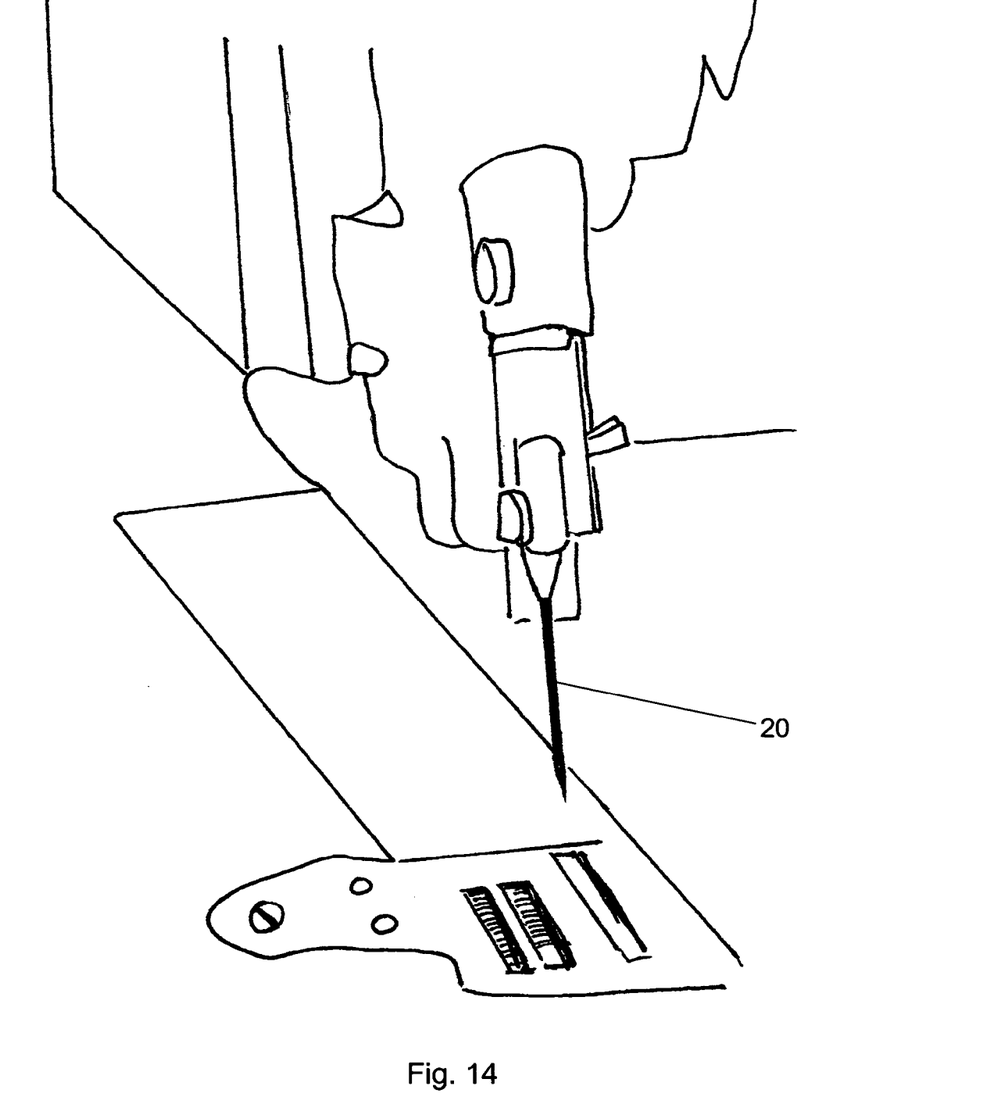
FIG. 14 shows another fragment of an overlock sewing machine for manufacturing Magic Floss, according to an embodiment of the present invention.

FIG. 14 illustrates a needle (20) without a presser foot that takes place when the Willcox and Gibbs overlock machines are deployed for manufacturing the Magic Floss.

Figure 15:
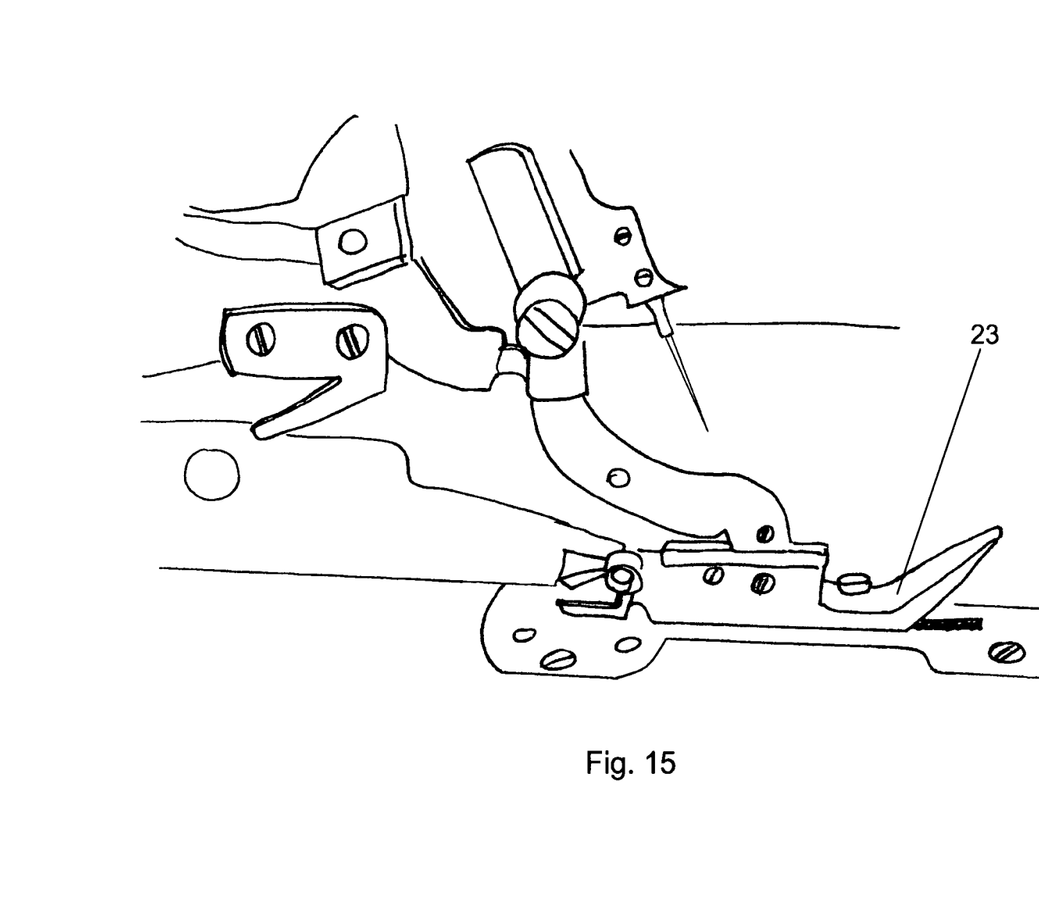
FIG. 15 shows another fragment of an overlock sewing machine for manufacturing Magic Floss, according to an embodiment of the present invention.

FIG. 15 is an illustration of adaptation of the Juki and Merrow overlock machines are deployed, in which case a presser foot (23) is used.

FIGS. 16a, 16b, 16c, 16d, and 17 are described hereinabove.

I claim:

1. A dental floss formed as a strand, including a plurality of threads braided with each other in a multi-looped manner so that collectively forming a volumetric knit structure; while being stretched along a straight line, said strand has a longitudinal axis, wherein said strand comprises:

a plurality of quasi-flat sections sequentially disposed and twisted in relation to each other along the longitudinal axis, wherein each said quasi-flat section is characterized with a plurality of quasi-flat cross-sections perpendicular to the longitudinal axis, wherein each said quasi-flat cross-section has a cross-sectional peripheral contour capable of being approximated to a rectangle-like figure having a width and a height, wherein the height is predeterminedly greater than the width, each said quasi-flat cross-section has a transversal axis parallel to the height, and, for any two adjacent quasi-flat sections, the corresponding transversal axes are disposed at a predetermined angle alpha in relation to each other, wherein each said quasi-flat cross-section encompasses a first number of thread pieces; and a plurality of knobs formed between and connecting each two adjacent said quasi-flat sections, wherein each said knob is characterized with a knob cross-section perpendicular to the longitudinal axis and encompassing a second number of thread pieces; and wherein the second number of thread pieces is greater than the first number of strand pieces, and said floss is made in any of the following forms: un-waxed, waxed, or impregnated with predetermined therapeutic agents.

2. The dental floss according to claim 1, wherein said angle alpha is substantially equal to 90 degrees.

3. The dental floss according to claim 1, wherein said threads are made of one of the following materials: PTFE, or woolly nylon, or a combination of PTFE and regular nylon, or silk, or polyester, or PTFE combined with soft metallic threads.

4. The dental floss according to claim 1, wherein said predetermined therapeutic agents include components selected from the group consisting of: ions of fluorine, sodium laurite, sodium perborate, alantoin, myrrh extract, charcoal, and xylitol.

5. The dental floss according to claim 1, wherein said floss is flavored with any of the following: mint, orange, lemon, cherry, strawberry, or vanilla.

6. The dental floss according to claim 1, wherein said floss is produced in a variety of predetermined colors.

7. The dental floss according to claim 1, wherein said floss is made as an endless loop.

8. The dental floss according to claim 1, wherein said floss is manufactured by means of a predeterminedly adapted conventional overlock machine.

9. The dental floss according to claim 1, wherein said floss is wound up on a spool, said spool is placed in a casing that has an aperture for pulling said floss out of said casing.

* * * * *